(12) United States Patent
Szul et al.

(10) Patent No.: US 8,257,558 B2
(45) Date of Patent: Sep. 4, 2012

(54) ALKYLENE OXIDE PURIFICATION SYSTEMS

(75) Inventors: John F. Szul, Hurricane, WV (US); James H. Mccain, Charlestown, WV (US); Floyd L. Pfeffer, Midland, MI (US); Harvey E. Andresen, Luling, LA (US); Phillip R. Fairchild, Luling, LA (US); Kent E. Newman, Scott Depot, WV (US)

(73) Assignee: Dow Technology Investments LLC, Midland, MI (US)

( * ) Notice: Subject to any disclaimer, the term of this patent is extended or adjusted under 35 U.S.C. 154(b) by 479 days.

(21) Appl. No.: 12/460,756

(22) Filed: Jul. 24, 2009

(65) Prior Publication Data

US 2010/0029962 A1 Feb. 4, 2010

Related U.S. Application Data

(60) Provisional application No. 61/137,485, filed on Jul. 31, 2008, provisional application No. 61/137,494, filed on Jul. 31, 2008, provisional application No. 61/137,517, filed on Jul. 31, 2008, provisional application No. 61/137,514, filed on Jul. 31, 2008, provisional application No. 61/137,493, filed on Jul. 31, 2008.

(51) Int. Cl.
*B01D 3/16* (2006.01)
*C07D 301/32* (2006.01)

(52) U.S. Cl. .......................... 203/82; 549/541

(58) Field of Classification Search .................. 549/541; 203/82
See application file for complete search history.

(56) References Cited

U.S. PATENT DOCUMENTS

| | | | |
|---|---|---|---|
| 2,615,901 A | 10/1952 | McClellan | |
| 2,697,104 A | 12/1954 | Lowe et al. | |
| 2,771,473 A | 11/1956 | Courter | |
| 2,775,600 A | 12/1956 | Maslan | |
| 2,815,650 A | 12/1957 | McIntire et al. | |
| 3,094,401 A | 6/1963 | Max | |
| 3,165,539 A | 1/1965 | Lutz | |
| 3,174,262 A | 3/1965 | Lutz | |
| 3,216,177 A | 11/1965 | Bracken et al. | |
| 3,398,062 A | 8/1968 | Tsao | |
| 3,418,338 A | 12/1968 | Gilman et al. | |
| 3,531,376 A | 9/1970 | Minoda et al. | |
| 3,729,899 A | 5/1973 | Cunningham | |
| 3,745,092 A | 7/1973 | Vanderwater | |
| 3,766,714 A | 10/1973 | Cunningham et al. | |
| 3,856,484 A * | 12/1974 | Cocuzza et al. | 95/191 |
| 3,867,113 A | 2/1975 | Foster et al. | |
| 3,904,656 A | 9/1975 | Broz | |
| 3,948,621 A | 4/1976 | Cocuzza et al. | |
| 3,964,980 A | 6/1976 | Ozero | |
| 4,033,617 A | 7/1977 | Cocuzza et al. | |
| 4,134,797 A | 1/1979 | Ozero | |
| 4,597,833 A | 7/1986 | N'eel et al. | |
| 4,845,296 A | 7/1989 | Ahmed et al. | |
| 4,966,657 A | 10/1990 | Delannoy et al. | |
| 4,983,260 A | 1/1991 | N'eel et al. | |
| 5,233,060 A | 8/1993 | Pendergast et al. | |
| 5,529,667 A | 6/1996 | Coffey | |
| 6,080,897 A | 6/2000 | Kawabe | |
| 6,123,812 A | 9/2000 | Bessling et al. | |
| 6,437,199 B1 | 8/2002 | Oka et al. | |
| 6,498,272 B1 | 12/2002 | Schröder et al. | |
| 6,833,057 B1 | 12/2004 | Bessling et al. | |
| 7,179,875 B2 | 2/2007 | Fuchs et al. | |
| 2004/0236049 A1 | 11/2004 | Fuchs et al. | |
| 2005/0103617 A1 | 5/2005 | Andreis et al. | |
| 2005/0277778 A1 | 12/2005 | Viswanathan et al. | |
| 2006/0264648 A1 | 11/2006 | Beekman et al. | |

FOREIGN PATENT DOCUMENTS

| | | |
|---|---|---|
| CZ | 104663 | 8/1962 |
| DE | 1165567 | 3/1964 |
| DE | 199 24 533 | 11/2000 |
| DE | 19924533 | 11/2000 |
| DE | 101 38 150 | 2/2003 |
| DE | 10138150 | 2/2003 |
| EP | 0 181 273 | 5/1986 |
| EP | 0181273 | 5/1986 |
| FR | 1 330 900 | 5/1963 |
| FR | 1330900 | 5/1963 |
| FR | 2 851 564 | 8/2004 |
| FR | 2851564 | 8/2004 |
| GB | 564646 | 10/1944 |
| GB | 589547 | 6/1947 |
| JP | 54-16416 | 2/1979 |
| JP | 54016416 | 2/1979 |
| JP | 62-12770 | 1/1987 |
| JP | 62012770 | 1/1987 |
| WO | WO 2003/055869 | 7/2003 |
| WO | WO 2004/056453 | 7/2004 |
| WO | WO 2006/120207 | 11/2006 |
| WO | WO 2006/120207 A1 | 11/2006 |
| WO | WO 2009/094103 | 7/2009 |
| WO | WO 2009/094103 A1 | 7/2009 |
| WO | WO 2009/105252 | 8/2009 |
| WO | WO 2009/105252 A1 | 8/2009 |

OTHER PUBLICATIONS

International Search Report and Written Opinion from related PCT Application PCT/US 2009/004295, dated Dec. 21, 2009 (16 pgs).
Viera, G.A., et al. "Lessons Learned from the Ethylene Oxide Explosion at Seadrift, Texas". Chem Eng. Progress. 89 (8), pp. 66-75 (1993).
Wankat, P.C. et al. "Two-Feed Distillation: Same-Composition Feeds with Different Enthalpies" Ind. Eng. Chem. Res. 1993, 32, 3061-3067.

(Continued)

*Primary Examiner* — Bernard Dentz
(74) *Attorney, Agent, or Firm* — Brooks, Cameron & Huebsch, PLLC

(57) ABSTRACT

Embodiments of the present disclosure provide processes, columns, and systems for removing acetaldehyde from alkylene oxide in a feed stream and for providing an alkylene oxide-water stream that can be directly transferred to a glycol reaction process. The alkylene oxide purification column includes a first section to convert a feed stream into a gas phase portion and a liquid phase portion and a second section located in the column above the first section to separate alkylene oxide from the acetaldehyde, water, and other impurities that enter the second section from the first section.

14 Claims, 3 Drawing Sheets

OTHER PUBLICATIONS

Cleveland et al. "Meteor Revolution" Hydrocarbon Engineering Oct. 2001 pp. 69-71.

Xiangyu, Z. "A Comparison of EO/EG Process Technologies" Sinopec Shanghai Engineering Co. Shanghai, 2006.

"U.S. Appl. No. 12/460,810, Notice of Allowance mailed Dec. 7, 2011", 12 pages.

"U.S. Appl. No. 12/460,755, Non Final office action mailed Dec. 6, 2011", 11 pages.

"U.S. Appl. No. 12/460,752, Non Final office action mailed Dec. 13, 2011", 15 pages.

"U.S. Appl. No. 12/460,775, Notice of Allowance mailed Jun. 8, 2011", 5 pages.

"U.S. Appl. No. 12/460,775, Notice of Allowance mailed Jul. 13, 2011", 5 pages.

\* cited by examiner

ALKYLENE OXIDE PURIFICATION SYSTEMS

This application claims priority to U.S. Provisional Application 61/137,485 filed Jul. 31, 2008, the specification of which is incorporated herein by reference, and is co-filed with co-owned U.S. patent application Ser. No. 61/137,494, entitled "Alkylene Oxide Recovery Systems" filed on Jul. 31, 2008, Ser. No. 61/137,517, entitled "Alkylene Oxide Recovery Systems" filed on Jul. 31, 2008, Ser. No. 61/137,514, entitled "Alkylene Oxide Purification Processes and Systems" filed on Jul. 31, 2008, and Ser. No. 61/137,493, entitled "Alkylene Oxide Recovery Systems" filed on Jul. 31, 2008.

FIELD OF THE DISCLOSURE

This disclosure relates to a distillation column for recovering alkylene oxide from a feed stream containing the same. More particularly, this disclosure relates to an alkylene oxide purification column for separating acetaldehyde from alkylene oxide in an impure feed stream.

BACKGROUND

Ethylene oxide is manufactured worldwide in amounts of several million tons per year. It can be prepared in large quantities by oxidizing ethylene with air or pure oxygen over a suitable catalyst, for example a silver-containing catalyst, at elevated temperature (e.g., one hundred (100) degrees Celsius (° C.) to five hundred (500)° C.) and at superatmospheric pressure (e.g., two (2) to twenty-five (25) atmospheres (atms)) whereby ethylene and oxygen react to form ethylene oxide.

The ethylene oxide production reactor effluent, which can include ethylene oxide, unconverted ethylene and oxygen, carbon dioxide, aldehydes, other low molecular weight hydrocarbons, and fixed gases such as argon and nitrogen, can be treated with water to remove the ethylene oxide. The ethylene oxide can then be further refined into a form with sufficient purity for industrial applications from the resulting mixture of ethylene oxide and water.

SUMMARY

Embodiments of the present disclosure provide processes, columns, and systems for removing acetaldehyde from alkylene oxide in a feed stream and for providing an alkylene oxide-water stream that can be directly transferred to a glycol reaction process. Embodiments are adaptable to commercial scale alkylene oxide production.

In some embodiments, an alkylene oxide purification column (AOPC) includes a first section to convert a feed stream including alkylene oxide, water, acetaldehyde, and other impurities into a gas phase portion of the feed stream including alkylene oxide, acetaldehyde, water, and other impurities and a liquid phase portion of the feed stream including alkylene oxide and water. The AOPC further includes a second section located in the column above the first section to separate alkylene oxide from the acetaldehyde, water, and other impurities that enter the second section from the first section. The second section includes a tray located at a bottom portion of the second section to collect alkylene oxide, acetaldehyde, and other impurities in a liquid phase, and a first side take-off located at the tray for removal of the alkylene oxide, acetaldehyde, and other impurities in the liquid phase, and a second side take-off located at a top portion of the second section for removal of a purified alkylene oxide exit stream.

In various embodiments, a process for separating acetaldehyde from alkylene oxide includes introducing a feed stream including alkylene oxide to a first section of an AOPC, where the column includes the first section and a second section located above the first section, and separating the feed stream into a gas phase portion of the feed stream, where the gas phase portion of the feed stream includes alkylene oxide, acetaldehyde, water, and other impurities, and a liquid phase portion of the feed stream including alkylene oxide and water, where the liquid phase portion exits the first section as an alkylene oxide-water stream. The process also includes separating the alkylene oxide from acetaldehyde, water, and other impurities that enter the second section from the first section to produce a purified alkylene oxide stream.

Definitions

As used herein, "distilling" and a "distillation process" refer to a process of separating compounds based on their differences in volatilities by vaporization and subsequent condensation, as for purification or concentration. In embodiments discussed herein, distillation can be performed on an aqueous mixture (i.e., feed stream) to purify, recover, and/or separate an alkylene (e.g., ethylene oxide), where the "aqueous mixture" can be defined as a mixture of an alkylene oxide, water, and other compounds in liquid form. As used herein, the terms "distill," "recover," "purify," and "separate" should be understood to refer to the distillation process as it is described herein.

As used herein, an "alkylene oxide purification column," "purification column," and/or "column" refers to, for example, a generally upright, cylindrical column or tower containing separation stages, such as trays and/or packing elements, where the trays and/or packing elements provide a surface area for a liquid and a gas to come into contact, facilitating mass transfer between the liquid and the gas. As will be appreciated, the column can also have other shapes and general orientations including a polygonal shaped column that is positioned in a horizontal orientation. The alkylene oxide purification column includes a first section and a second section separated by a tray, such as a chimney tray. The alkylene oxide purification column, or column, as discussed herein, can have a diameter ranging from, for example, 65 centimeters (cm) to 6 meters (m) and have a height ranging from, for example, 6 m to 60 m or more.

As used herein, a "heat exchanger" refers to a device built for heat transfer from one fluid to another whether the fluids are separated by a solid wall so that they never mix, or the fluids are directly contacted. In addition, "sensible heat" refers to the heat absorbed or evolved by a substance during a change of temperature that is not accompanied by a change of state. Thus, a "sensible heat heat exchanger" refers to a heat exchanger that transfers heat from one fluid to another without changing the state of the heating fluid.

As used herein, "latent heat" refers to an amount of energy released or absorbed by a substance during a change of state, such as during the condensation of steam. Thus, a "latent heat heat exchanger" refers to a heat exchanger that transfers heat from one fluid to another during a change of state of the heating fluid (e.g., steam).

As used herein a "separation stage" is defined as a volume, device or combination of devices in a distillation apparatus within or at which phases are brought into intimate contact, where mass transfer occurs between the phases tending to bring them to equilibrium, and where the phases can then mechanically separated. For the various embodiments, each tray of a tray tower and/or packing of a packed tower having a height equivalent to a theoretical plate ("HETP") is a separation stage, as these are the locations where fluids are brought into intimate contact, interphase diffusion occurs, and the fluids are separated. As such, the number of trays in a distillation apparatus can also be attributed to an equivalent number of separation stages that are obtained by using packing. For the various embodiments, the terms separation stage, tray and/or packing having a HETP can be used interchangeably, unless otherwise stated to the contrary.

As appreciated by one skill in the art, determining a number of equilibrium stages (theoretical trays) for use in a distillation apparatus can be calculated based on the material balances and equilibrium considerations of the compounds (e.g., ethylene oxide, water, and other compounds in liquid form) to be separated in the substance (e.g., the aqueous mixture of the present disclosure). The efficiency of the separation stage, and therefore the number of separation stages that are actually used, can be determined by the mechanical design used and the condition of operation for the distillation apparatus. For the various embodiments provided herein, the number of equilibrium stages (or theoretical trays) could be used in place of the number of separation stages provided in the present disclosure through the use of the efficiency of the separation stage of the distillation apparatus.

As used herein, a "condenser" is a device that converts vapor into liquid. In embodiments discussed herein, a gas phase portion of a feed stream can enter the condenser, where some compounds in the gas phase portion of the feed stream condense into liquid while other compounds pass through the condenser and remain in the gas phase. Also, as used herein, a "reflux condenser" is a condenser such that vapor over a boiling liquid condenses and can flow back into the vessel containing the boiling liquid to prevent the vessel's contents from boiling dry.

As used herein, "a," "an," "the," "at least one," and "one or more" are used interchangeably. The terms "comprises" and variations thereof do not have a limiting meaning where these terms appear in the description and claims. Thus, for example, a first section located in an alkylene oxide recovery column to convert a portion of "a" feed stream to a gas phase portion can be interpreted to mean that the alkylene oxide recovery column includes "one or more" feed streams.

The term "and/or" means one, more than one, or all of the listed elements.

As used herein, the term "about" may not be limited to the precise value specified. In at least one instance, the variance indicated by the term "about" can be determined with reference to the precision of the measuring instrumentation.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

DETAILED DESCRIPTION

Figure 1:
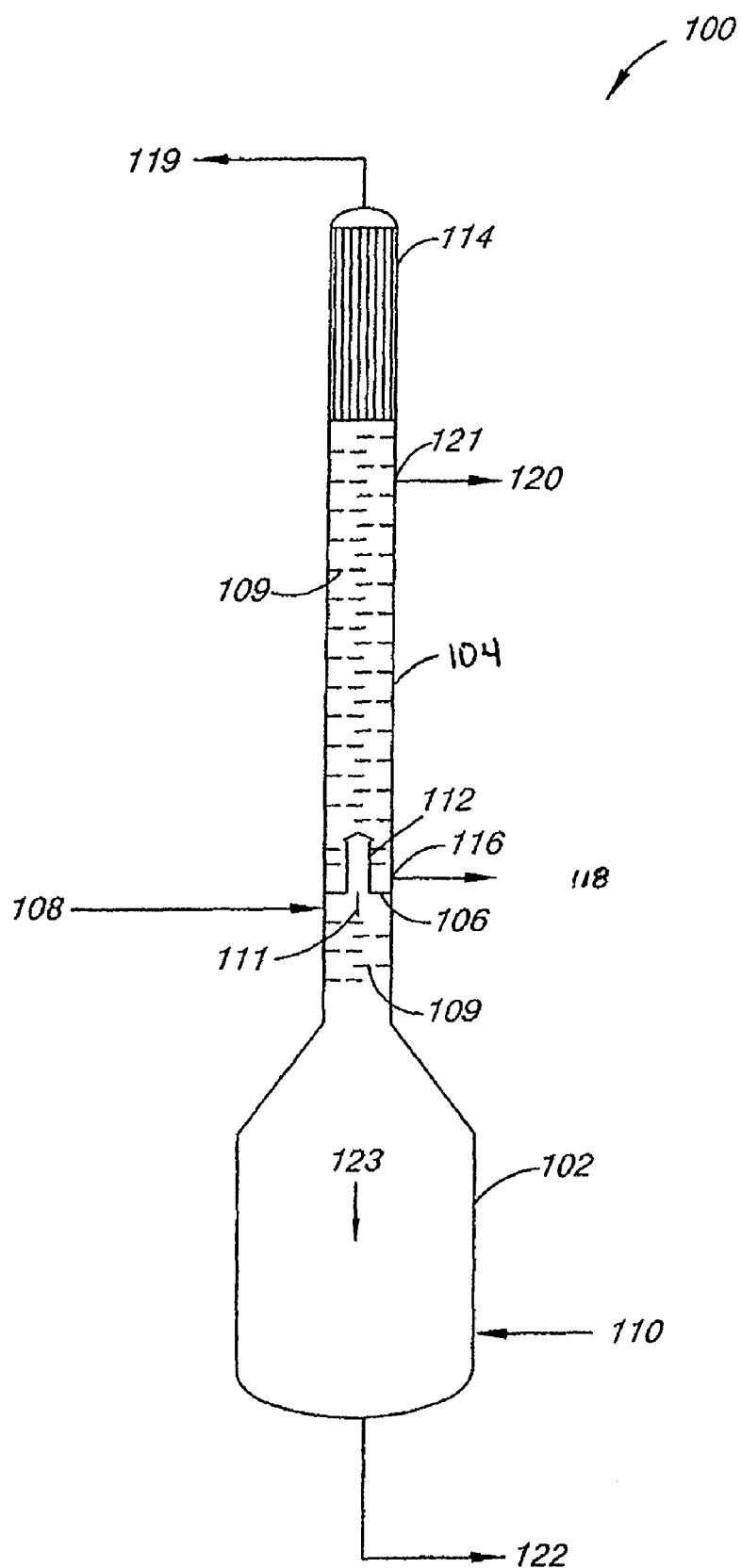
FIG. 1 provides an embodiment of an alkylene oxide purification column of the present disclosure.

Embodiments of the present disclosure include columns, processes, and systems for separating acetaldehyde from alkylene oxide in a feed stream and for providing an alkylene oxide-water stream that can be directly transferred to a glycol reaction process. Embodiments are adaptable to commercial scale alkylene oxide production.

As discussed herein, embodiments of the present disclosure include recovering alkylene oxide from a feed stream. Preferred embodiments include recovering ethylene oxide from the feed stream. As such, embodiments of the present disclosure as they relate to ethylene oxide will be described herein. However, one of skill in the art will appreciate that embodiments of the present disclosure also apply to other alkylene oxides including propylene oxide, butylene oxide, methylene oxide, among others.

The system embodiments include a heat exchanger and an ethylene oxide purification column (EOPC) operably connected to the heat exchanger.

Embodiments of the present disclosure achieve separation of ethylene oxide and impurities (e.g., acetaldehyde) in a single distillation column utilizing an aqueous mixture as a feed stream, a first section of the column to remove a portion of ethylene oxide and other components from the feed stream, and a second section to separate ethylene oxide from acetaldehyde, water, and other impurities that enter the second section from the first section, as discussed further herein. In addition, the use of the EOPC can produce an ethylene oxide-water stream that can be fed directly to a glycol reactor. Also, the use of a single column can, in some embodiments, result in lower equipment cost when building a system as described herein, as compared to systems having two or three distillation columns for purifying ethylene oxide. In some embodiments, pure ethylene oxide can be taken off the EOPC as a side stream while ethylene oxide containing light impurities, such as carbon dioxide, oxygen, nitrogen, and argon, among others, can be taken off the column as a top stream.

Several steps can be performed to obtain the aqueous mixture that is used as the feed stream to the EOPC. As described herein, the steps to produce ethylene oxide and to use the produced ethylene oxide in further reactions can occur in one place, for example, in an ethylene oxide processing plant. The various steps, however, can also occur in separate facilities.

In addition, in an ethylene oxide production unit, the ethylene oxide production processes can be interlinked with ethylene oxide recovery processes. In certain cases where the ethylene oxide production unit is operated along with downstream product manufacturing units such as, for example an ethylene glycol manufacturing unit, the ethylene oxide processes can also be interlinked with ethylene glycol manufacturing processes to maximize energy utilization, which in turn can lower production costs.

Alkylenes (olefins) employed in the process of this disclosure can be characterized by the following structural formula (I):

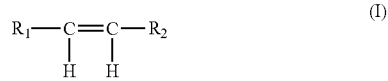

wherein $R_1$ and $R_2$ are each individually selected from hydrogen and lower monovalent radicals, preferably $C_1$-$C_6$ alkyl radicals including methyl, ethyl, propyl, butyl, and higher homologues having up to six carbon atoms. Preferably, $R_1$ and $R_2$ are each individually selected from hydrogen, methyl, and ethyl. More preferably, each $R_1$ and $R_2$ is hydrogen, and the preferred olefin is ethylene. The corresponding alkylene oxides produced in the process of this disclosure are preferably characterized by the following structural formula (II):

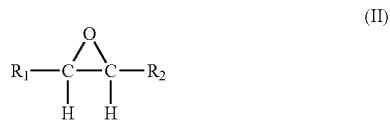

wherein $R_1$ and $R_2$ are identified herein in connection with the reactant olefin. Most preferably, the alkylene oxide is ethylene oxide (i.e., $R_1$ and $R_2$ are both hydrogen).

Oxygen may be provided to the process as pure molecular oxygen. Alternatively, oxygen may be provided as an oxygen-containing gas, where the gas further contains one or more gaseous components, for example, gaseous diluents such as nitrogen, helium, methane, and argon, which are essentially inert with respect to the oxidation process. In some embodiments, a suitable oxygen-containing gas is air. Additionally, the oxygen-containing gas may contain one or more of the following gaseous components: water, carbon dioxide, and various gaseous promoters and/or gaseous by-product inhibitors, as discussed herein.

The relative volumetric ratio of alkylene to oxygen in the feed stock gas may range in accordance with any of such known conventional values. Typically, the volumetric ratio of alkylene to oxygen in the feed stock may vary from about 2:1 to about 6:1. Likewise, the quantity of inert gases, diluents, or other gaseous components such as water, carbon dioxide, and gaseous promoters and gaseous by-product inhibitors, may vary in accordance with known conventional ranges as found in the art.

The present disclosure is applicable to epoxidation reactions in any suitable reactor, for example, fixed bed reactors, fixed bed tubular reactors, continuous stirred tank reactors (CSTRs), and fluid bed reactors, a wide variety of which are well known in the art. The desirability of recycling unreacted feed, employing a single-pass system, or using successive reactions to increase ethylene conversion by employing reactors in a series arrangement can also be readily determined by those skilled in the art.

The particular mode of operations selected can be dictated by process economics. Conversion of alkylene (olefin), preferably ethylene, to alkylene oxide, preferably ethylene oxide, can be carried out, for example, by continuously introducing a feed stream containing alkylene (e.g., ethylene) and oxygen, or an oxygen-containing gas, to a catalyst-containing reactor at a temperature of from about 200 degrees Celsius (° C.) to about 300° C., and a pressure which may be in a range of from approximately 5 atmospheres (506 kilopascals (kPa)) to approximately 30 atmospheres (3,040 kPa), depending on the mass velocity and productivity desired. Residence times in large scale reactors can be on the order of about 0.1 to about 5 seconds. In some embodiments, the feedstock can be passed over a catalyst in the reactor, for example, a silver-containing catalyst. The resulting alkylene oxide, preferably ethylene oxide, can then be separated and recovered from the reaction products using further processes.

In nearly all processes containing ethylene oxide and water, some degree of reaction between ethylene oxide and water to form ethylene glycol can occur. The reactivity is highest in systems with higher temperatures and longer residence times. In most cases, the formation of ethylene glycol in the EOPC is not ideal as the reaction conditions are not ideal and the formation of monoethylene glycol (MEG) can lead to further side reactions. For instance, MEG can react with additional ethylene oxide to form higher glycols, such as diethylene glycol and triethylene glycol, or glycols can be oxygenated to form the resulting glycol aldehyde with each side reaction resulting in lower overall process efficiency to MEG. Monoethylene glycol can be produced from ethylene via the intermediate ethylene oxide, where ethylene oxide reacts with water to produce MEG in a glycol reactor, as discussed herein. High selectivity to MEG is desirable since MEG is an important raw material for industrial applications, including the use of MEG in the manufacture of polyester resins, films, and fibers. In addition, MEG is important in the production of antifreezes, coolants, aircraft anti-icers and deicers, and solvents.

Ethylene glycol can be produced by the (catalyzed or uncatalyzed) hydrolysis of ethylene oxide. Ethylene oxide hydrolysis can proceed with either acid or base catalysis or through an uncatalyzed hydrolysis in a neutral medium. Acid catalyzed hydrolysis activates the ethylene oxide by protonation for the reaction with water. Base catalyzed hydrolysis, however, results in considerably lower selectivity to ethylene glycol, producing diethylene glycol and higher glycols (e.g., triethylene and tetraethylene glycols) in addition to the ethylene glycol. Ethylene glycol monoethers can be manufactured by the reaction of an alcohol with ethylene oxide. Also, ethanolamine can be manufactured by the reaction of ethylene oxide with ammonia. See, for example, U.S. Pat. No. 4,845,296.

In some instances, to produce ethylene oxide, a feedstock of ethylene and pure oxygen, or air, after blending with cycle gas, can enter an ethylene oxide reactor, along with other compounds. The ethylene oxide reactor can be a fixed bed reactor or a fluid-bed reactor, as discussed herein. In some embodiments, a ballast gas (e.g., methane, nitrogen) can be added to the feed stock gas to increase the lower flammability limit of the inlet gas, enhancing the safety and stability of the system. In addition, in some embodiments, a small quantity of ethylene dichloride or other chlorine-containing compounds can be introduced into the feed stock gas to decrease side reactions and to improve the selectivity of ethylene oxidization.

In some embodiments, the per-pass conversion of ethylene to ethylene oxide can be low (e.g., on the order of 1 percent or less). The gaseous reaction effluent thus formed contains dilute concentrations of ethylene oxide along with unreacted ethylene and oxygen, aldehydes, acid impurities, nitrogen, and argon, among other components. In some embodiments, the aldehydes can include formaldehyde and acetaldehyde. In some embodiments, the per-pass conversion of ethylene to ethylene oxide can range from 5 percent to 25 percent.

The ethylene oxide can be separated and recovered from the gaseous reaction effluent. For example, the gaseous reaction effluent from the reactor can be scrubbed with an absorbent, such as water, to form an aqueous mixture containing ethylene oxide in an absorber column. The absorption of ethylene oxide in water can recover ethylene oxide from unreacted ethylene, oxygen, and/or other gaseous components (e.g., carbon dioxide, nitrogen, argon). The remaining gaseous materials can then be recycled as cycle gas to be mixed with the feedstock of ethylene and pure oxygen, and fed to the ethylene oxide reactor for the production of ethylene oxide as gaseous reaction effluent.

The aqueous mixture containing ethylene oxide from the absorber column can then be passed to a stripper (e.g., a stripping column) where steam is introduced to remove ethylene oxide product as overhead. The overhead product from the stripper, containing carbon dioxide, ethylene oxide, gaseous inerts, and water vapor, can then be cooled to partially condense the ethylene oxide and water, and the resulting mixture of vapor and liquid, or just vapor, can be passed to an ethylene oxide reabsorber, in which the uncondensed ethylene oxide vapor is reabsorbed in water. From the reabsorption step, an aqueous mixture can be obtained which contains reabsorbed ethylene oxide and aldehydic impurities, such as formaldehyde and acetaldehyde, as well as dissolved carbon dioxide and other gaseous impurities. This aqueous mixture is then further purified using the aqueous mixture as the feed stream in embodiments of the present disclosure.

In the Figures herein, as will be appreciated, elements shown in the embodiments herein can be added, exchanged, and/or eliminated so as to provide any number of additional embodiments of processes and/or systems. In addition, as will be appreciated, the proportion and the relative scale of the elements provided in the figure is intended to illustrate the embodiments of the present invention, and should not be taken in a limiting sense.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. In addition, the description herein of an element and/or component provided for one or more Figures is applicable to and associated with other Figures illustrating the same element and/or component number but which do not necessarily provide the express description thereof. So, for example, when element "10" in FIG. 1 is expressly discussed herein this express discussion is also applicable to element "10" in the other Figs. where it may appear.

FIG. 1 provides a schematic representation of an embodiment of an ethylene oxide purification column (EOPC) 100, or column 100, according to the present disclosure. As shown in the embodiment of FIG. 1, the column 100 can include a first section 102 and a second section 104 located in the column 100, where the second section 104 is located above the first section 102, and the two sections 102, 104 are separated by a tray 106, such as a chimney tray or other device or construction that allows vapor to pass up and that prevents liquid from passing down from the second section 104 to first section 102.

In some embodiments, the first section 102 can be located in a lower half of the column 100 and the second section 104 can be located in an upper half of the column 100. As discussed herein, embodiments of the present disclosure can be used to purify the aqueous mixture of ethylene oxide produced from the reabsorption step, referred to hereinafter as the feed stream.

The operating conditions within the column 100 can be adjusted according to processing conditions. In various embodiments, the column can be operated at atmospheric pressure. In some embodiments, the column 100 can be operated slightly above atmospheric pressure. In certain embodiments, there may be a gradient in pressure across the column 100, and this gradient may be a gradual change across the column and/or various sections of the column 100 or may be an abrupt pressure change.

The first section 102 can have a number of components, as discussed herein, including inlets and outlets. In FIG. 1, the feed inlet is provided at an upper portion of the first section 102 to introduce the feed stream 108 into the first section 102.

The feed stream 108 produced from absorbing the dilute ethylene oxide mixture in the absorber, stripper, and subsequent reabsorber can be introduced to the first section 102. In some embodiments, the feed stream 108 can enter the first section 102 in liquid phase. Additionally, in various embodiments, the feed stream 108 can enter the first section 102 as a combination of a liquid phase and a gas phase. Examples of possible compounds in addition to water and ethylene oxide in the feed stream 108 include ethylene glycol, oligo(ethylene glycol)s, aldehydes, such as formaldehyde and/or acetaldehyde, carbon dioxide, and methane, among other compounds.

In some embodiments, the feed stream 108 to be purified includes, in each case based on its weight, from about 5 to about 95 percent by weight, preferably from about 5 to about 50 percent by weight, and more preferably about 5 to about 20 percent by weight ethylene oxide and from about 95 to about 5 percent by weight, preferably from about 95 to about 50 percent by weight, and more preferably about 95 to about 80 percent by weight of water. The feed stream 108 can further include aldehydes in a range of about 0.1 mole parts per million (mol ppm) to about 500 mol ppm. For example, the feed stream 108 can include acetaldehyde in a range of about 1 mol ppm to about 20 mol ppm. It will be appreciated that the sum of the ingredients of the feed stream 108 is 100 percent in each case.

As discussed herein, in some embodiments, the feed stream 108 can be separated into a gas phase portion of the feed stream and a liquid phase portion of the feed stream in the first section 102. However, there are a number of ways to achieve the separation of the feed stream 108.

For example, as will be appreciated by one skilled in the art, the design and operation of the column 100, including the first and second sections 102, 104, can depend on the composition of the feed stream 108, as well as the composition of the desired products, among other things. In some instances, for example, with a binary component feed, analytical methods such as the McCabe Thiele method or the Fenske equation can be used to determine the number of equilibrium stages to use to achieve the desired separation of the feed stream 108. For a multi-component feed stream, simulation models can be used for both design (e.g., to determine the number of equilibrium stages needed in order to achieve the desired separation) and operation (e.g., to determine the optimum operating conditions). In addition, once the number of equilibrium stages is determined, one skilled in the art can use experimentation to determine the number of separation stages (e.g., the actual number of trays or height of packing) to use in a column to achieve the desired separation.

In some embodiments, the first section 102 of the present disclosure can include separation stages (e.g., trays, dumped packing, and/or structured packing) in order to perform the separation of the feed stream 108. In some embodiments, the first section 102 can include a combination of different types of separation stages, such as trays and packing. The trays can be of a type of plate commonly found in purification columns, including sieve plates, bubble-cap plates, and/or valve plates, among others. In some embodiments, the distance between each tray can vary. In addition, in embodiments using packing, the packing material can be random dumped packing such as, for example Raschig rings, Pall rings, or Bialecki rings in metal and/or ceramic. The packing material can also be structured sheet-metal packing such as those known and commercially available for example under the designations Gempak® (Kock-Glitsch, LP, Dallas, Tex., U.S.A) and/or Mellapak® (Gebr. Sulzer, Winterthur, Switzerland).

In embodiments where random packing is employed, the total required height of packing to provide the required number of separation stages can be determined by multiplying the number of calculated equilibrium stages by the Height Equivalent to a Theoretical Plate, or HETP. The HETP is a value of the height of packing that will give the same separation as an equilibrium stage. As known to one skilled in the art, the HETP can vary depending on the type of packing selected.

In some embodiments, the total height of packing can be split into one or more zones with vapor-liquid redistributors in between the zones, for example, to accommodate height limitations due to packing structural integrity or to accommodate feed streams or product streams. In some embodiments, packing may offer the advantage of a lower pressure drop as compared to trays, although consideration must also be given to the cost difference arising from the choice of trays versus packing.

In embodiments where the first section 102 has trays (e.g., a tray tower), the trays can be physical devices which are used to provide contact between an upflowing vapor and a down-flowing liquid inside the first section 102. In some instances, the efficiency of a tray can be lower than that of a theoretical, 100 percent efficient equilibrium stage, hence, the first section 102 can have more actual, physical trays (separation stages) than the required number of theoretical vapor-liquid equilibrium stages.

In some embodiments, each tray can be at a different temperature and pressure, where the bottom tray can have the highest pressure and temperature. In some embodiments, while proceeding upwards along the first section 102, the temperature and pressure decreases for each succeeding stage. In some instances, the vapor-liquid equilibrium for each feed component of the feed stream 108 in the first section 102 can react in a unique way to the different pressure and temperature conditions at each of the stages. That means, in some embodiments, each component establishes a different concentration in the vapor and liquid phases at each of the stages, resulting in the separation of components in the feed stream 108.

As discussed herein, the number of equilibrium stages needed in order to achieve a desired separation can be calculated using the McCabe Thiele method, the Fenske equation, or simulation models. As one skilled in the art will appreciate, once the number of equilibrium stages in the first section 102 is determined using the methods mentioned, the range of separation stages can be determined using routine experimentation.

As shown in FIG. 1, the feed stream 108 can enter the first section 102 at a top portion of the first section 102, above a number of separation stages 109 (e.g., trays and/or packing) provided in the first section 102. In various embodiments, the feed stream 108 can enter the first section 102 below the separation stages 109, or at a specific separation stage.

In addition, a stripping gas 110 can be introduced into the first section 102 of the column 100. For example, the stripping gas 110 can be introduced at a lower portion of the first section 102 to contact the feed stream 108 in a countercurrent fashion with the stripping gas 110. In some embodiments, the stripping gas 110 can be steam or hot water. Steam stripping can be an economic method of separating ethylene oxide from the feed stream 108.

Although the embodiment in FIG. 1 illustrates a stripping gas 110 being introduced into the first section, in some embodiments, steam can be generated within the first section 102 by making use of a heating mechanism placed internally or externally to the column 100. For example, a steam heated reboiler can be employed to heat water in the bottom of the first section 102 and boil it.

In some embodiments, the stripping gas 110 and the separation stages 109 included in the first section 102 can remove ethylene oxide from the feed stream 108 by converting a portion of the feed stream 108 to a gas phase portion 111 of the feed stream 108. As used herein, the "gas phase portion of the feed stream" is the portion of the feed stream 108 that is produced in the first section 102 and can, in some embodiments, enter the second section 104 directly as a vapor, as discussed herein. In some embodiments, the gas phase portion 111 of the feed stream 108 can enter a condenser located in the first section 102, as discussed further herein. The gas phase portion 111 of the feed stream 108 can include ethylene oxide, water, acetaldehyde, and other impurities. In addition, the gas phase portion 111 of the feed stream 108 can include water that enters the first section 102 as a part of the feed stream 108 as well as water that enters the first section 102 as a part of the stripping gas 110.

As shown in FIG. 1, in some embodiments, the gas phase portion 111 of the feed stream 108 can flow from the first section 102 to the second section 104 through a tray 106, such as a chimney tray. As used herein, a "chimney tray" is a tray designed in such a way that it will allow vapor to rise through it, but it can prevent liquid from passing down through it by accumulating the down-flowing liquid on a collection tray. Thus, a chimney tray 106 can be used when the objective is to let vapor pass through a tray and collect the liquid coming down to the tray.

In some embodiments, the chimney tray 106 can be a solid tray of metal with a chimney 112, or standpipe, topped by a hat to keep liquid from raining down through the standpipe. A "hat," as used herein, refers to a cover that is loosely connected to the standpipe that can allow vapor to flow up and out of the standpipe, while preventing liquid from entering the standpipe from the second section 104. A "standpipe," or chimney, as used herein, is an open pipe which extends through the tray and some distance above the tray so that liquid can stand and accumulate on the tray.

As will be appreciated, the chimney tray 106 may additionally enhance distribution of an up-flowing vapor through the column 100, where the column 100 may contain separation stages (e.g., trays, dumped packing, structured packing, or a mixture of trays and packing). In addition, the chimney tray 106 can be designed to overflow the collected liquid back into the first section 102 via the chimney 112 during upset conditions. As used herein, the term "upset conditions," is defined as the conditions in which there is a disturbance and/or deviation from a normal functioning of the process.

In some embodiments, the gas phase portion 111 of the feed stream 108 can enter the second section 104 by passing through the chimney tray 106. In addition, in some embodiments where the second section 104 includes either packing or a mixture of trays and packing, the chimney 112 can be designed such that the top of the chimney 112 extends past some of the packing and/or trays in the second section 104 of the column 100.

The second section 104 can include separation stages 109 to separate ethylene oxide from acetaldehyde, water, and other impurities that enter the second 104 section from the first section 102. In the embodiment shown in FIG. 1, the second section 104 can separate ethylene oxide from acetaldehyde contained in the gas phase portion 111 of the feed stream 108. As appreciated by one skilled in the art, acetaldehyde and ethylene oxide can be difficult to separate due to the relative closeness of the boiling points of each compound. Specifically, ethylene oxide has a boiling point of about 10.4° C., while acetaldehyde has a boiling point of about 20.85° C. Due to the difficulty of separating ethylene oxide from acetaldehyde, the second section 104 of the column can include an increased amount of separation stages 109 as compared to the first section 102. For example, the second section 104 of the column can include about 20 separation stages to about 200 separation stages. In contrast, the first section 102 can include about 1 separation stages to about 10 separation stages.

In order to perform the separation in the second section 104, heat is provided to the chimney tray 106, as well as to the separation stages 109 throughout the second section 104 of the column 100. In addition, the second section 104 can include a condenser 114 located at a top portion of the second section 104 to condense certain compounds that enter the second section 104 from the first section 102. For example, the condenser 114 can condense ethylene oxide entering the second section 104, as well as other compounds including water, formaldehyde, acetaldehyde, and other impurities. In some embodiments, the condenser 114 can provide a liquid reflux to the second section 104 comprised of the condensed compounds.

In this way, the chimney tray 106 can collect the liquid reflux containing water, ethylene oxide, acetaldehyde, and other impurities in a liquid phase to be removed from the second section 104 at a first side take-off 116 located at the chimney tray 106 as a purge stream 118. In some embodiments, the purge stream 118 can include about 60 percent of the acetaldehyde from the feed stream 108, and at least 80 percent of the acetaldehyde in the gas phase portion 111 of the feed stream 108.

In some embodiments, the column 100 can be operated in such a way as to produce a purge stream 118 that is small enough as to allow the purge stream 118 to be disposed of or destroyed with minimal ethylene oxide loss. For example, in various embodiments, the purge stream 118 can include ethylene oxide in a range of about 0 to about 5 mole percent ethylene oxide.

Alternatively, in some embodiments, the column 100 can be operated in such a way as to produce a purge stream 118 that contains ethylene oxide in an amount that is uneconomical to dispose of or destroy. In such embodiments, the purge stream 118 can either be transferred to a separate column for continued separation in order to recover the ethylene oxide in the purge stream 118, or be routed to a small processing facility which converts the contained ethylene oxide to glycol before recovering the glycol in a refining system.

As discussed herein, in some embodiments, ethylene oxide can be separated from the gas phase portion 111 of the feed stream 108 in the second section 104 of the column 100. Most of the ethylene oxide separated from the gas phase portion 111 of the feed stream 108 can become a purified ethylene oxide exit stream 120, while a small portion can become part of the liquid reflux that becomes the purge stream 118, as discussed herein. In some embodiments, the purified ethylene oxide stream 120 can be removed from the second section 104 of the column 100 at a second side-take off 121 located at a top portion of the second section 104. For example, the purified ethylene oxide exit stream 120 can be removed above the trays and/or packing 109 in the second section 104.

As discussed herein, the second section 104 can include a condenser 114 located at a top portion of the second section 104. In some embodiments, the second side take off 121 can be located below the condenser 114. In addition, in various embodiments, the second side take-off 121 can be part of the condenser 114. In other words, the purified ethylene oxide exit stream 120 can be condensed in the condenser 114 and removed from the condenser 114, and thus removed from the second section 104 of the column 100.

In addition, while ethylene oxide can be removed from the column 100 as the purified ethylene oxide exit stream 120, ethylene oxide including light impurities, such as carbon dioxide, oxygen, nitrogen, and argon, among others, can be removed from the top of the column 100 as a light impurities stream 119.

As discussed herein, the feed stream 108 entering the first section 102 of the column 100 can be separated into a gas phase portion 111 and a liquid phase portion 123. The liquid phase portion 123 can be removed from the bottom portion of the first section 102 as an ethylene oxide-water stream 122. In some embodiments, the ethylene oxide-water stream can have a composition including at most 10 weight percent ethylene oxide, based on total weight of the ethylene oxide-water stream 122. Preferably, the ethylene oxide-water stream 122 can include ethylene oxide in a range of about 1 to about 10 weight percent, based on total weight of the ethylene oxide-water stream 122, and water in a range of about 90 to about 99 weight percent, based on total weight of the ethylene oxide-water stream 122. In various embodiments, the ethylene oxide-water stream 122, or liquid phase portion of the feed stream 208, can include between about 20 to about 90 percent of the ethylene oxide contained in the feed stream 108 fed to the first section 102.

In some embodiments, the column 100 is operated in such a way as to produce the ethylene oxide-water stream 122 with a composition suitable to feed the ethylene oxide-water stream 122 without further purification to a glycol reactor, where ethylene oxide is converted to ethylene glycol by reaction with water. As appreciated by one skilled in the art, acetaldehyde is known to be a precursor for various compounds, such as crotonaldehyde and/or glycol esters, which can contribute to poor glycol quality. For example, high acetaldehyde levels in the ethylene oxide-water stream 122 can lead to the production of purified MEG with an out-of-specification ultraviolet (UV) transmittance measurement and/or an out-of-specification total carbonyls measurement. Thus, reduction in acetaldehyde levels in the ethylene oxide-water stream 122 is desirable, as described in embodiments of the present disclosure. In such embodiments, the ethylene oxide-water stream 122 can include between about 1 and about 65 percent of the contained acetaldehyde in the feed stream 108, based on total weight of the ethylene oxide-water stream 122.

Figure 2:
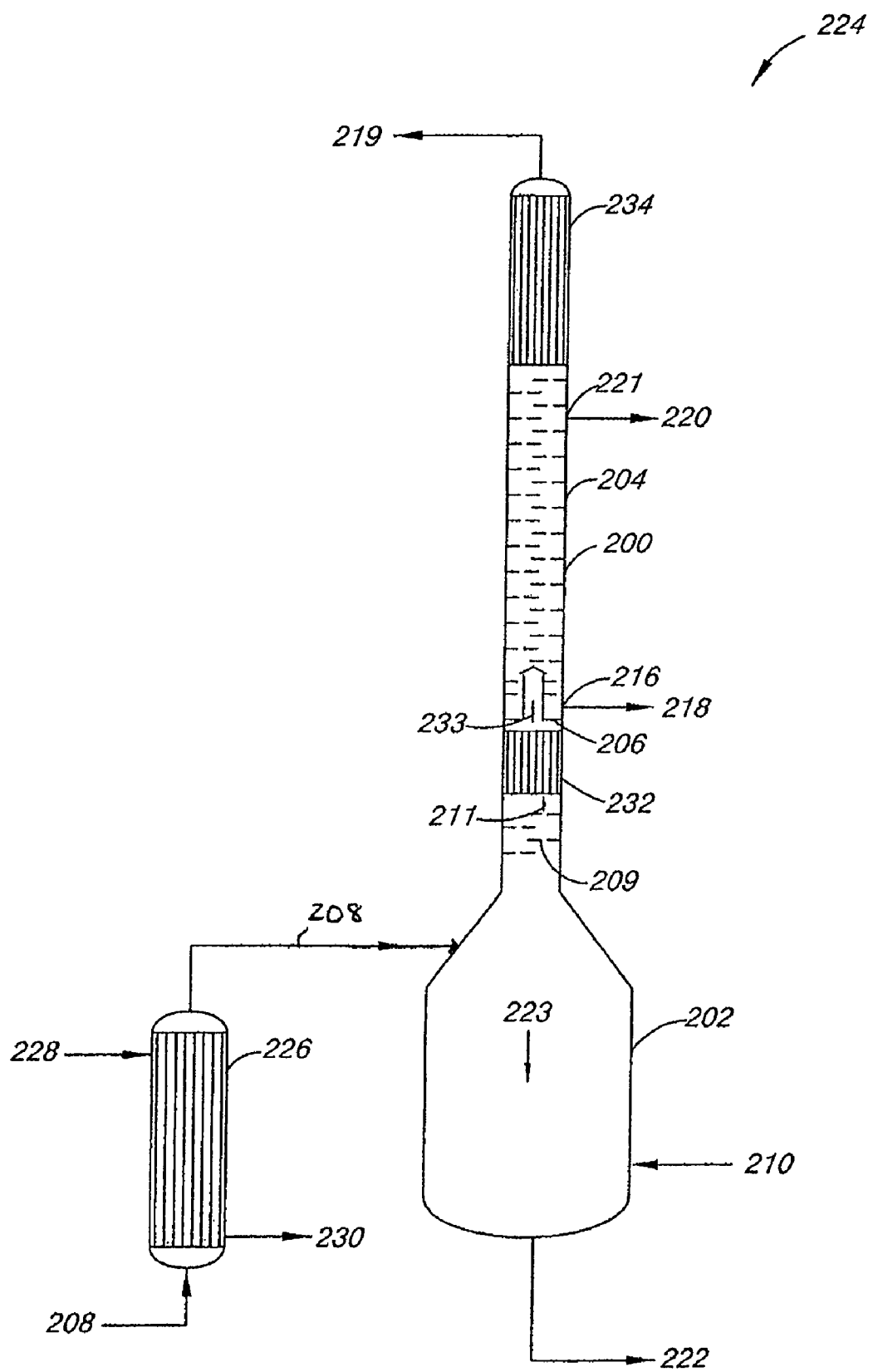
FIG. 2 provides an embodiment of a system of the present disclosure.

FIG. 2 illustrates an embodiment of a system according to the present disclosure. As shown in FIG. 2, the system 224 includes a heat exchanger 226 and a column 200, as described herein. The column includes a first section 202 and a second section 204 separated by a chimney tray 206.

In the embodiment shown in FIG. 2, the feed stream 208 produced from adsorbing the dilute ethylene oxide mixture in the absorber, stripper, and subsequent reabsorber can be introduced to the heat exchanger 226 to heat the feed stream 208. The heat exchanger 226 can allow for the integration of low-energy, or low temperature, streams into the process. For example, the heat exchanger 226 can heat the low temperature feed stream 208 before it is fed into the column 200, where the feed stream 208 is heated to a boiling point to thus distill ethylene oxide and other components from the feed stream 208. In some embodiments, the heat exchanger 226 can be a predominantly sensible heat heat exchanger, for example, a shell and tube heat exchanger or a plate heat exchanger.

In some embodiments, the use of a sensible heat heat exchanger, as defined herein, can allow heat to be added to the feed stream 208 while limiting the maximum temperature that the feed stream 208 can reach to the temperature of the liquid used on the heat input side of the heat exchanger. As used herein, "sensible heat" refers to the heat absorbed or evolved by a substance during a change of temperature that is not accompanied by a change of state. Thus, a "sensible heat heat exchanger" refers to a heat exchanger that transfers heat from one fluid to another without changing the state of the heating fluid. The use of a sensible heat heat exchanger can also reduce the use of high pressure steam as the heating medium in the heat exchanger 226. Reducing the use of high pressure steam, as compared to a low pressure steam as provided herein, can increase the safety of heating the ethylene oxide-containing feed stream 208 since ethylene oxide is a reactive compound with a sensitivity to high temperature. The use of a sensible heat heat exchanger can also allow for energy integration between the heat exchanger 226 and other areas in an ethylene oxide processing plant where heat is in excess, by routing an excess hot stream to the heat exchanger 226 to heat the feed stream 208, and subsequently cool the excess hot stream.

In additional embodiments, the heat exchanger 226 can be a latent heat heat exchanger, as discussed herein, where low pressure steam can be used as the heating fluid. As used herein, the low pressure steam can be supplied at a temperature that is incrementally higher than the feed stream 208 entering the heat exchanger 226. For the various embodiments, the incrementally higher temperature of the low pressure steam can be about 5 to 10° C. higher than the feed stream 208 entering the heat exchanger 226. Examples of low pressure steam values can include, but are not limited to 1-500 psia (pounds-force per square inch absolute), with 5-50 psia and/or 10-30 psia condensing pressures being suitable value ranges.

In various embodiments using a shell and tube heat exchanger, the heat exchanger 226 can be operated using countercurrent-flow, using a heat exchange fluid 228 (e.g., water or low pressure steam) entering the heat exchanger 226 at a high temperature at the top of the heat exchanger 226. As the fluid 228 flow heats the feed stream 208, energy is transferred from the fluid 228 to the feed stream 208, in effect cooling the fluid 228. The cooled heat exchange fluid 230, in some embodiments, can exit the heat exchanger 102 from the side of the heat exchanger 102 at the bottom, as shown in FIG. 2. In some embodiments, the heat exchanger 226 can be operated using a parallel flow.

Although the heat exchanger 226 is illustrated in FIG. 2 showing the feed stream 208 entering the bottom of the heat exchanger 226 and flowing up the heat exchanger 226, the feed stream 208 can also flow through the heat exchanger 226 from the top to the bottom. The heat exchange fluid 228 entrance and exit points can be correspondingly modified to heat the feed stream 208. Other heat exchanger 226 arrangements are also possible.

Examples of other heat exchanger 226 arrangements and/or configurations can include, but are not limited to, an insertion type reboiler and/or an internal reboiler. For the various embodiments, the insertion type reboiler and/or the internal reboiler can be positioned in situ at least partially within the first section 202 below the separation stages 209, where it can be used to provide heat to at least partially vaporize (e.g., provide boil-up) the liquid in the bottom of the column 200. For the various embodiments, the insertion type reboiler and/ or an internal reboiler can utilize latent heat or sensible heat in heating the liquid content of the column 200. For the various embodiments, it is also possible to use both the heat exchanger 226 and the insertion type reboiler or the internal reboiler to provide the boil-up in the column 200. For the various embodiments, it is also possible to operate the column 200 with either the insertion type reboiler and/or the internal reboiler as the only source of heat for the column 200 boil-up. For the various embodiments, the use of the insertion type reboiler and/or an internal reboiler as the only source of heat for the column 200 boil-up might be due to a greater need for heat than can be, or is desired to be, transferred in the heat exchanger 226.

For the various embodiments, the insertion type reboiler and/or an internal reboiler can be positioned below the bottom liquid level of the first section 202 to vaporize liquid to generate column vapor for good vapor/liquid contacting and multistage separation. Providing boil-up in this manner is in contrast to diverting the liquid from the bottom of the first section 202 to an external reboiler, via a recirculation loop, the use of which may raise safety concerns due to the presence of ethylene oxide in the diverted liquid stream. For the various embodiments, using an insertion type reboiler and/or an internal reboiler, instead of a typical external circulating loop and reboiler containing ethylene oxide, can help to increase the inherent safety of the system by reducing the inventory of ethylene oxide outside the column 200 and can help to reduce the opportunity for ethylene oxide to be exposed to high temperature heating medium if the circulation loop would fail to operate properly.

In some embodiments, the feed stream 208 entering the first section 202 of the column 200 can be at a predetermined temperature or in a predetermined temperature range, where the predetermined temperature is chosen based on the boiling point of the feed stream. For example, the feed stream 208 can enter the first section 202 at a temperature in a range of about 30° C. to about 140° C. In some embodiments, the heat exchanger 226 can be operated to heat the feed stream 208 to the predetermined temperature or predetermined temperature range. For example, the heat exchanger 226 can be operated to heat the feed stream 208 entering the heat exchanger 226 at a temperature in a range of about 70° C. to about 120° C. By heating the feed stream 208 prior to the feed stream 208 entering the first section 202, less energy is spent heating the feed stream 208 inside the first section 202. As appreciated by one skilled in the art, different operating parameters of the heat exchanger 226 can be varied to heat the feed stream 208 to the predetermined temperature, including the type of heat exchange fluid 228, the flow rate of the heat exchange fluid 228, and/or the inlet temperature of the heat exchange fluid 228, among others.

As shown in FIG. 2, the feed stream 208 can enter the first section 202 of the column 200 at a top portion of the first section 202. As discussed herein, the first section 202 can include a number of separation stages 209 to aid in the conversion of the feed stream 208 to a gas phase portion 211 of the feed stream 208 and a liquid phase portion 223 of the feed stream 208. As shown in FIG. 2, the feed stream 208 can enter the first section 202 below the separation stages included in the first section 202. However, as discussed herein, the feed stream 208 can also enter the first section 202 at other locations at the top portion of the first section 202.

As shown in the embodiment illustrated in FIG. 2, the first section 202 can also include a condenser 232 located at the top portion of the first section 202, above the separation stages 209. The gas phase portion 211 of the feed stream 208 can flow to the condenser 232 to cool and partially condense the gas phase portion 211 of the feed stream 208, producing an ethylene oxide rich vapor stream 233 that enters the second section 204 through the chimney tray 206 and a liquid reflux stream that is in physical communication with the first section 202.

Similar to the gas phase portion 211 of the feed stream 208, the ethylene oxide rich vapor stream 233 can include ethylene oxide, acetaldehyde, water, and other impurities that flow into the second section 204. However, the condenser 232 can partially condense portions of the gas phase portion 211 of the feed stream 208, therefore, the amount of water entering the second section 204 can be considerably less as compared to the embodiment shown in FIG. 1. In addition, the liquid reflux from the condenser 232 can mix with the liquid phase portion 223 of the feed stream 208 that is removed from the first section 202 as an ethylene oxide-water stream 222, as discussed herein.

As illustrated in FIG. 2, in some embodiments, the condenser 232 can be located a top portion of the first section 202 integral with the column 200. In such embodiments, the condenser 232 can be a reflux condenser. A reflux condenser can return condensed vapors directly to the first section 202, and any noncondensable gases (e.g., the gas phase portion 211 of the feed stream 208) can be released at the top of the condenser 232. In some embodiments, a portion of the heat removed from the condenser 232 can be usefully employed in other parts of the ethylene oxide purification column 200 process, and/or in other parts of the ethylene oxide processing plant.

In some embodiments, the condenser 232 can be separate from the column 200, where the gas phase portion 211 of the feed stream 208 can be routed to the condenser 232. In such embodiments, the system 224 can include process streams to provide a pathway for the liquid reflux stream from the condenser 232 to be returned to the first section 202, and the ethylene oxide rich vapor stream to be routed to the second section 204 of the column 200.

As discussed herein, the ethylene oxide rich vapor stream 233 can be introduced to the second section 204 of the column through the chimney tray 206. In the second section 204, the ethylene oxide can be separated from acetaldehyde, water, and other impurities that enter the second section 204 from the first section 202. Specifically, the ethylene oxide rich vapor stream 233 can be separated into a liquid phase purge stream 218 and a purified ethylene oxide exit stream 220 that can be removed from the column 200 via a first side take-off 216 and a second side take-off 221, respectively.

As discussed herein, the second section of the column 200 can include separation stages 209, a condenser 234 positioned at a top portion of the second section 204, and heat input to the chimney tray 206 to separate ethylene oxide from acetaldehyde, water, and other impurities that enter the second section 204 from the first section 202.

Figure 3:
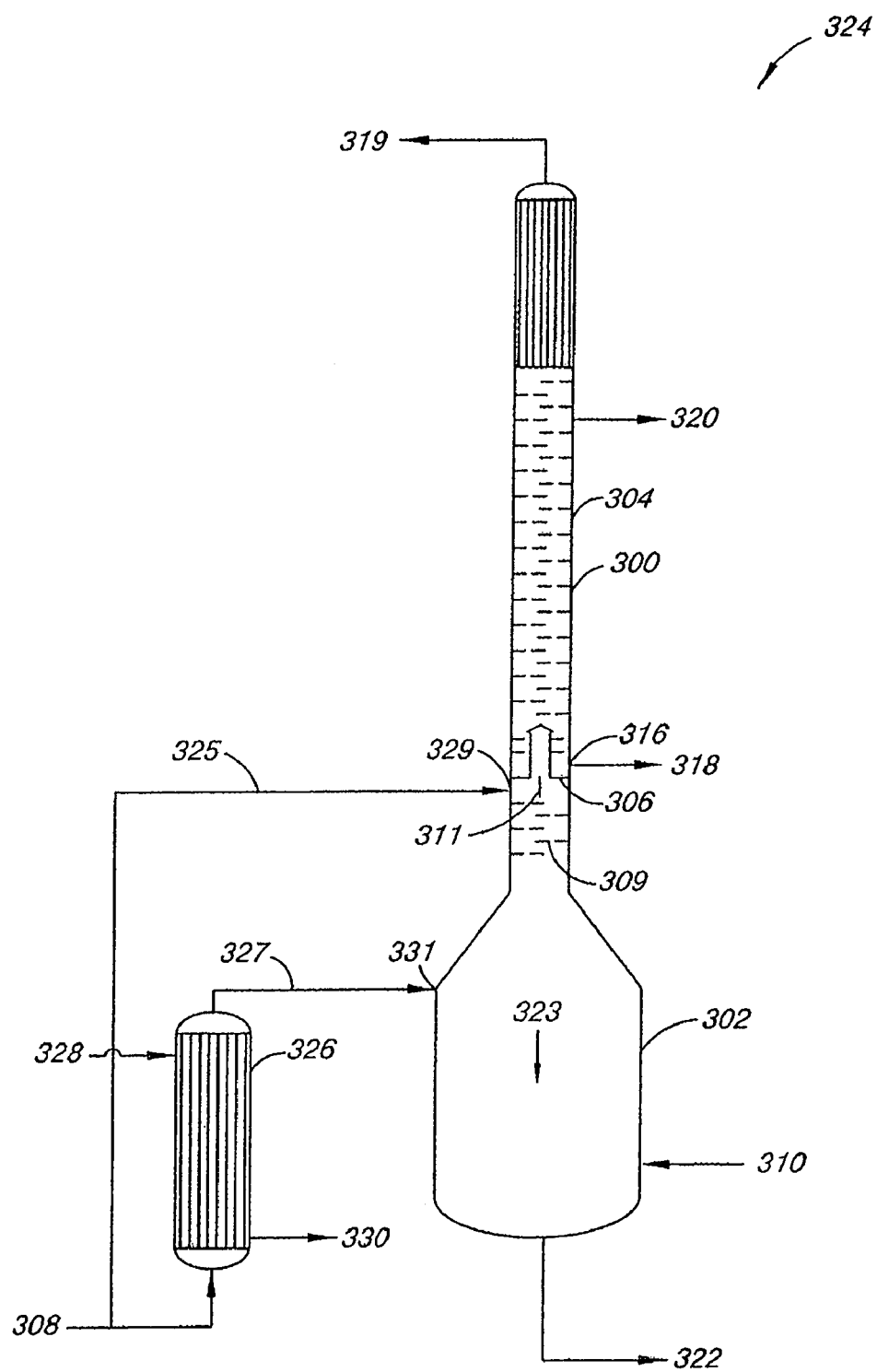
FIG. 3 provides an embodiment of a system of the present disclosure.

FIG. 3 illustrates an embodiment of a system 324 according to the present disclosure. As discussed herein, the system 324 includes a heat exchanger 326 and a column 300 according to the present disclosure.

As shown in FIG. 3, in some embodiments, the feed stream 308 can be separated into a first portion 325 of the feed stream 308 and a second portion 327 of the feed stream 308. In some embodiments, the feed stream 308 can be such that the first portion 325 is about 25 volume percent of the feed stream 308 before the separation, and the second portion 327 can be about 75 volume percent of the feed stream 308 before the separation. Other relative proportions of the first portion 325 and second portion 327 are also possible.

In various embodiments, the feed stream 308 can be separated before the heat exchanger 326, where the first portion 325 is routed around the heat exchanger 326 and enters the first section 302 of the column 300 at a first inlet 329 located above the separation stages 309 included in the first section 302. The second portion 327 of the feed stream 308 can be routed to the heat exchanger 326, where the second portion 327 of the feed stream 308 can be heated using the heated fluid 328, as discussed herein. The heated, second portion 327 of the feed stream 308 can then enter the first section 302 of the column 300 at a second inlet 331 located below the separation stages 309 included in the first section 302.

By splitting the feed stream 308 into two portions and providing the same to the first section 302 above and below the separation stages 309, the cool feed stream entering the first inlet 329 can condense portions of the heated second portion 327 of the feed stream 308 entering the second inlet 331 to form the gas phase portion 311 of the feed stream 308. In this way, water entering the first section 302 in the first 325 and second 327 portions of the feed stream 308, as well as from the stripping gas 310, can be condensed, preventing water from entering the gas phase portion 311 of the feed stream 308. Thus, by splitting the feed stream 308, the first section 302 operates similar to an embodiment where the first section 302 includes a condenser at the top portion of the first section 302, while saving the equipment and processing costs of having to install and operate a condenser inside the first section 302.

As discussed herein, the gas phase portion 311 can enter the second section 304 through the chimney tray 306, where the gas phase portion 311 can be separated to form a purge stream 318 and a purified ethylene oxide exit stream 320. In addition, the liquid phase portion 323 of the feed stream 308 can be removed from the first section 302 and routed directly to a glycol reactor, as discussed herein.

For the various embodiments, the ethylene oxide separated according to the present disclosure can be processed to provide further downstream products, such as, for example, 1,2-diols, 1,2-diol ethers, 1,2-carbonates, and alkanolamines. Since the present disclosure provides improvements to the separation and purity of the ethylene oxide, it is contemplated that the improvements provided herein will carry forward to provide improvements to these downstream processes and/or products. Improved methods for the production of 1,2-diols, 1,2-carbonates, 1,2-diol ethers and alkanolamines are thus also provided herein.

The conversion of ethylene oxides into 1,2-diols or 1,2-diol ethers may comprise, for example, reacting the ethylene oxide with water, suitably in the presence of an acidic or basic catalyst. For example, for preferential production of the 1,2-diol over the 1,2-diol ether, the ethylene oxide may be reacted with a tenfold molar excess of water, in a liquid phase reaction in the presence of an acid catalyst, e.g., 0.5-1.0 wt % sulfuric acid, based on the total reaction mixture, at 50-70° C. at 1 bar absolute, or in a gas phase reaction, at 130-240° C. and 20-40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternatively, 1,2-diol ethers may be prepared by converting the ethylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of ethylene oxide distilled according to the present disclosure into alkanolamines may comprise, for example, reacting the ethylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

It is to be understood that the above description has been made in an illustrative fashion, and not a restrictive one. Although specific embodiments have been illustrated and described herein, those of ordinary skill in the art will appreciate that other component arrangements can be substituted for the specific embodiments shown. The claims are intended to cover such adaptations or variations of various embodiments of the disclosure, except to the extent limited by the prior art.

In the foregoing Detailed Description, various features are grouped together in exemplary embodiments for the purpose of streamlining the disclosure. This method of disclosure is not to be interpreted as reflecting an intention that any claim requires more features than are expressly recited in the claim. Rather, as the following claims reflect, inventive subject matter lies in less than all features of a single disclosed embodiment. Thus, the following claims are hereby incorporated into the Detailed Description, with each claim standing on its own as a separate embodiment of the invention.

Specific Embodiments of the Disclosure

The following examples are provided for illustrative purposes only and are not intended to limit the scope of the present disclosure.

EXAMPLE 1

Comparative Example

In this Example, a distillation column having separation stages and a condenser located at a top portion of the column is modeled in ASPENPLUS® Release 2004.1 available from Aspen Technology, Inc. (Cambridge, Mass. USA). A feed stream enters the column at a lower portion of the column containing a reboiler, and a condenser is located at a top portion of the column. Purified ethylene oxide is withdrawn from a top portion of the column as a side stream, an ethylene oxide-water stream is removed from the column at a bottom portion of the column, and a light impurities stream is removed from the column at a top portion of the column. Table 1 provides the contents of the various inlet and outlet streams.

TABLE 1

|  | Feed Stream | Ethylene Oxide-Water Stream | Light Impurity Stream | Purified Ethylene Oxide Exit Stream |
| --- | --- | --- | --- | --- |
| Ethylene Oxide (kg/hr) | 46,913 | 17,137 | 691 | 29,085 |
| Acetaldehyde (kg/hr) | 4.2 | 4.0 | 0.0 | 0.3 |
| Water (kg/hr) | 434,710 | 434,710 | 0.0 | 0.0 |

EXAMPLE 2

In this Example, a column is provided according to embodiments of the present disclosure. A reflux condenser is located in the first section below a chimney tray. The column is modeled in ASPEN as two separate RADFRAC blocks. The first section is modeled with 6 separation stages with the feed stream inlet on stage 6, or the bottom stage. Process steam is also fed at stage 6 to provide additional heat to the first section. A partial vapor condenser is specified in the RADFRAC block to model the reflux condenser. A reflux ratio of 3 is specified. A vapor distillate rate of 30,500 is achieved. The gas phase portion of the first section is fed to a second RADFRAC block which models the second section of the column. The second section is specified with a reboiler, partial vapor condenser, 40 separation stages, a reflux ratio of 200, and a purge stream flow of 200 kilograms per hour (kg/hr). The gas phase portion of the feed stream is specified to enter separation stage 38 and the purified ethylene oxide stream is taken off as a side stream at separation stage 3 at a rate of 29,350 kg/hr. Table 2 provides the compositional make-up of the streams entering and exiting the column as modeled in ASPEN.

TABLE 2

|  | Feed Stream | Ethylene Oxide-Water Stream | Stream Entering Second Section | Purge Stream | Purified Ethylene Oxide Exit Stream | Light Impurities Stream |
| --- | --- | --- | --- | --- | --- | --- |
| Temperature (° C.) | 110.7 | 118.2 | 41.65 | 43.45 | 38.3 |  |
| Acetaldehyde (mole fraction) |  |  |  | 0.013 | 3 ppm |  |
| Ethylene Oxide (mole fraction) | 0.04 | 0.01 | 0.999 | 0.93 | 0.99 | 0.99 |
| Water (Mole Fraction) | 0.96 | 0.98 | 0.00 | 0.06 |  |  |
| Ethylene oxide (kg/hr) | 47,862 | 17,370 | 30,491 | 192 | 29,350 | 949 |

TABLE 2-continued

|  | Feed Stream | Ethylene Oxide-Water Stream | Stream Entering Second Section | Purge Stream | Purified Ethylene Oxide Exit Stream | Light Impurities Stream |
|---|---|---|---|---|---|---|
| Water (kg/hr) | 434,759 | 454,614 | 5 | 5 | 0 | |
| Acetaldehyde (kg/hr) | 4.3 | 1.5 | 2.8 | 2.7 | 0.1 | |

In this example, the first section is specified to provide a low purge stream flow in the second section. Although the purge stream flow is low, it is relatively high in ethylene oxide concentration. However, as can be seen in Table 2, the amount of acetaldehyde in the ethylene oxide-water stream modeled to be leaving the first section is drastically reduced as compared to the ethylene oxide-water stream provided in the comparative example described in Example 1. In addition, the excess water in the ethylene-oxide water stream relative to the feed stream is due to stripping gas injection (e.g., steam).

EXAMPLE 3

In this example, the column conditions are modified to allow more water to enter the second section of the column, and exit via the purge stream, diluting the ethylene oxide concentration. In this example, a reflux condenser is located in the first section below the chimney tray. The column is modeled in ASPEN as two separate RADFRAC blocks, similar to Example 2. The first section is modeled with 6 separation stages, with the feed stream entering the column on stage 6 (i.e., bottom stage). A stripping gas is also fed at separation stage 6. A partial vapor condenser is specified in the RADFRAC block to model the reflux condenser. A reflux ratio of 2 was specified. A vapor distillate rate of 30,500 kg/hr is achieved. The gas phase portion of the feed stream from the first section is fed to a second RADFRAC block which models the second section of the column. The second section is specified with a reboiler, partial vapor condenser, 40 separation stages, a reflux ratio of 250, and a purge stream flow of 170 kg/hr. The gas phase portion of the first section is specified to enter separation stage 38 and the purified ethylene oxide stream is taken off as at a side take-off at separation stage 3 at a rate of 29,350 kg/hr. Table 3 provides the compositions of the streams entering and exiting the column.

In this example, the second section is specified to provide a low purge stream flow in the second section, but the conditions are modified to provide a lower ethylene oxide concentration in the purge stream. To achieve this, more water is passed through the chimney and the base temperature of the second section is increased by about 30° C., as compared to Example 2. As can be seen in Table 3, the amount of acetaldehyde is the ethylene oxide-water stream is drastically reduced versus Example 1. In addition, the excess water in the ethylene-oxide water stream relative to the feed stream is due to stripping gas injection (e.g., steam).

EXAMPLE 4

In this example, the first section does not include a condenser. The column is modeled in ASPEN as two separate RADFRAC blocks. The first section is modeled with 6 separation stages with the feed on stage 1 (i.e., top stage). A stripping gas is also fed to the first section at separation stage 6. The feed stream temperature and stripping gas injection is adjusted to provide the desired vapor flow through the chimney tray. The gas phase portion of the feed stream is fed to the second RADFRAC block which models the second section of the column. The second section is specified with a reboiler, partial vapor condenser, 40 separation stages, and a reflux ratio of 120 and a top vapor rate of 1,000 kg/hr. The gas phase portion of the feed stream is specified to enter separation stage 35 and the purified ethylene oxide is taken off at a side take-off at separation stage 3 at a rate of 29,350 kg/hr. Table 4 presents the compositions of each stream entering and exiting the column.

TABLE 3

|  | Feed Stream | Ethylene Oxide-Water Stream | Stream Entering Second Section | Purge Stream | Purified Ethylene Oxide Exit Stream | Light Impurities Stream |
|---|---|---|---|---|---|---|
| Temperature (° C.) | 110.7 | 118.2 | 43.07 | 72.07 | 38.3 | 38.09 |
| Acetaldehyde (mole fraction) | | | | 0.007 | 9 ppm | |
| Ethylene Oxide (mole fraction) | 0.04 | 0.015 | 0.989 | 0.066 | 0.999 | 0.999 |
| Water (Mole Fraction) | 0.96 | 0.984 | 0.011 | 0.925 | | |
| Ethylene oxide (kg/hr) | 47,891 | 17,538 | 30,353 | 25 | 29,350 | 979 |
| Water (kg/hr) | 434,759 | 454,477 | 142 | 142 | 0 | |
| Acetaldehyde (kg/hr) | 4.2 | 1.2 | 3.0 | 2.8 | 0.3 | |

TABLE 4

|  | Feed Stream | Ethylene Oxide-Water Stream | Stream Entering Second Section | Purge Stream | Purified Ethylene Oxide Exit Stream | Light Impurities Stream |
|---|---|---|---|---|---|---|
| Temperature (° C.) | 100 | 118.6 | 100.04 | 81.02 | 38.3 | 38.09 |
| Acetaldehyde (mole fraction) |  |  |  | 165 ppm | 10 ppm |  |
| Ethylene Oxide (mole fraction) | 0.04 | 0.015 | 0.6697 | 0.051 | 0.999 | 0.9992 |
| Water (Mole Fraction) | 0.96 | 0.984 | 0.330 | 0.9486 |  |  |
| Ethylene oxide (kg/hr) | 47,912 | 16,732 | 31,179 | 830 | 29,350 | 999 |
| Water (kg/hr) | 434,760 | 448,332 | 6,288 | 6,288 | 0 |  |
| Acetaldehyde (kg/hr) | 4.2 | 1.3 | 3.0 | 2.7 | 0.3 |  |

In this example, the second section is specified to provide a low purge stream flow in the second section, but the conditions are modified to provide a lower ethylene oxide concentration in the same stream. To achieve this, more water is passed through the chimney and the base temperature of the second section is increased by about 40° C. versus that shown in Example 2. As can be seen in the Table 4, the amount of acetaldehyde in the first section ethylene oxide-water stream is drastically reduced versus that shown in Example 1. In addition, the excess water in the ethylene-oxide water stream relative to the feed stream is due to stripping gas injection (e.g., steam).

EXAMPLE 5

In this example, a condenser is not included in the first section. The column is modeled in ASPEN as two separate RADFRAC blocks. The first section is modeled with 6 separation stages with the feed at stage 1 (i.e., top stage). A stripping gas is also fed to the first section, at separation stage 6. The feed temperature and stripping gas injection is adjusted to provide the desired vapor flow through the chimney tray. The gas phase portion of the feed stray is fed to the second RADFRAC block, which models the second section of the column. The second section is specified with a reboiler, partial vapor condenser, 40 separation stages, and a reflux ratio of 140 and a light impurities stream rate of 1,600 kg/hr. The gas phase portion of the feed stream is specified to enter separation stage 35 and the purified ethylene oxide stream is taken off as a side take-off located at separation stage 3 at a rate of 29,350 kg/hr. Table 5 presents the compositions of each stream entering and exiting the column.

TABLE 5

|  | Feed Stream | Ethylene Oxide-Water Stream | Stream Entering Second Section | Purge Stream | Purified Ethylene Oxide Exit Stream | Light Impurities Stream |
|---|---|---|---|---|---|---|
| Temperature (° C.) | 100 | 118.6 | 100.04 | 108.95 | 38.3 | 38.11 |
| Acetaldehyde (mole fraction) |  |  |  | 186 ppm | 1 ppm |  |
| Ethylene Oxide (mole fraction) | 0.04 | 0.015 | 0.6697 | 0.019 | 0.999 | 0.9996 |
| Water (Mole Fraction) | 0.96 | 0.984 | 0.330 | 0.980 |  |  |
| Ethylene oxide (kg/hr) | 47,977 | 16,731 | 31,246 | 297 | 29,350 | 1,599 |
| Water (kg/hr) | 434,737 | 448,296 | 6,301 | 6,301 | 0 |  |
| Acetaldehyde (kg/hr) | 4.2 | 1.3 | 3.0 | 2.9 | 0.03 |  |

This example is similar to Example 4, except that the base temperature of the second section is increased further to reduce the amount of ethylene oxide in the purge stream. As can be seen in Table 5, the amount of acetaldehyde in the ethylene oxide-water stream removed from the first section is drastically reduced versus that in Example 1. In addition, the excess water in the ethylene-oxide water stream relative to the feed stream is due to stripping gas injection (e.g., steam).

EXAMPLE 6

In this example, the first section does not include a condenser. The column is modeled in ASPEN as two separate RADFRAC blocks. The first section is modeled with 6 separation stages. The feed stream fed to the first section is modified so that 25 percent of the feed bypasses a heat exchanger. The bypassed feed stream enters the first section at separation stage 1 (i.e., top stage), and the preheated feed enters the column at separation stage 6 (i.e., bottom stage). A stripping gas is also fed to the first section at separation stage 6. The feed temperature and stripping gas injection is adjusted to provide a desired vapor flow through the chimney tray. The gas phase portion of the feed stream from the first section is fed to a second RADFRAC block which models the second section of the column. The second section is specified with a reboiler, partial vapor condenser, 40 separation stages, a reflux ratio of 200, and a purge stream rate of 1,300 kg/hr. The gas phase portion of the feed stream is specified to enter separation stage 38 and the purified EO is taken off at a side take-off at separation stage 3 at a rate of 29,350 kg/hr. Table 6 presents the compositions of each stream entering and exiting the column.

TABLE 6

|  | Feed Stream | Bypassed Feed Stream to Stage 1 | Ethylene oxide-water stream | Stream Entering Second Section | Purge stream | Purified Ethylene Oxide Exit Stream | Light impurities Stream |
|---|---|---|---|---|---|---|---|
| Temperature (° C.) | 110.7 | 52.53 | 118.0 | 67.7 | 94.92 | 38.3 | 38.1 |
| Acetaldehyde (mole fraction) |  |  |  |  | 794 ppm | 16 ppm |  |
| Ethylene Oxide (mole fraction) | 0.04 | 0.04 | 0.015 | 0.9114 | 0.031 | 0.999 | 0.998 |
| Water (Mole Fraction) | 0.96 | 0.96 | 0.984 | 0.088 | 0.967 |  |  |
| Ethylene oxide (kg/hr) | 33,433 | 14,328 | 17,467 | 30,293 | 96 | 29,350 | 848 |
| Water (kg/hr) | 304,336 | 130,430 | 453,465 | 1,201 | 1,201 | 0 |  |
| Acetaldehyde (kg/hr) | 2.97 | 1.3 | 1.4 | 2.9 | 2.4 | 0.5 |  |

In this example, the split feed stream is employed to replace the functionality of the reflux condenser utilized in Examples 2 and 3. As can be seen in the data table, the amount of acetaldehyde in the ethylene oxide-water stream is drastically reduced versus Example 1. In addition, the excess water in the ethylene-oxide water stream relative to the feed stream is due to stripping gas injection (e.g., steam).

What is claimed:

1. An ethylene oxide purification column, comprising:
a first section located in the column to convert a feed stream including ethylene oxide, water, acetaldehyde, and other impurities into a gas phase portion of the feed stream including ethylene oxide, acetaldehyde; water, and other impurities and a liquid phase portion of the feed stream including ethylene oxide and water; and
a second section located in the column above the first section to separate ethylene oxide from the acetaldehyde, water, and other impurities that enter the second section from the first section, where the second section includes:
a tray located at a bottom portion of the second section to collect ethylene oxide, acetaldehyde, and other impurities in a liquid phase and a first side take-off located at the tray for removal of the ethylene oxide, acetaldehyde, and other impurities in the liquid phase; and
a second side take-off located at a top portion of the second section for removal of a purified ethylene oxide exit stream.

2. The column of claim 1, where the first section includes a condenser located at a top portion of the first section integral with the column.

3. The column of claim 1, where the first section includes a condenser located outside the column.

4. The column of claim 1, where the first section includes at least one separation stage in a top portion of the first section.

5. The column of claim 4, where the first section includes an inlet for the feed stream located above the at least one separation stage.

6. The column of claim 4, where the first section includes an inlet for the feed stream located below the at least one separation stage.

7. The column of claim 4, where the first section includes a first inlet for a first portion of the feed stream located above the at least one separation stage and a second inlet for a second portion of the feed stream located below the at least one separation stage.

8. The column of claim 1, where the liquid phase portion of the feed stream exits the first section through an outlet as an ethylene oxide-water stream, and where the ethylene oxide-water stream contains at least 35 percent of the ethylene oxide in the feed stream and has a composition including at most 10 weight percent ethylene oxide, based on a total weight of the ethylene oxide-water stream.

9. The column of claim 1, where the second section includes a condenser located at a top portion of the second section integral with the column, where the purified ethylene oxide exit stream exits the condenser at the second side take-off.

10. The column of claim 1, where the second section includes at least one separation stage to separate ethylene oxide from acetaldehyde in the gas phase portion of the feed stream.

11. A system to purify ethylene oxide, comprising:
a heat exchanger including a feed stream exit stream; and
an ethylene oxide purification column operably connected to the heat exchanger, where the feed stream exit stream is connected to the column as a feed stream, and where the column includes:
a first section located in the column to convert the feed stream including ethylene oxide, water, acetaldehyde, and other impurities into a gas phase portion of the feed stream including ethylene oxide, acetaldehyde, water, and other impurities and a liquid phase portion of the feed stream including ethylene oxide and water; and
a second section located in the ethylene oxide purification column above the first section to separate ethylene oxide from the water, acetaldehyde, and other impurities that enter the second section from the first section, where the second section includes:
a tray located at a bottom portion of the second section to collect ethylene oxide, acetaldehyde, and other impurities in a liquid phase and a first side take-off located at the tray for removal of the ethylene oxide, acetaldehyde, and other impurities in the liquid phase; and a second side take-off located at a top portion of the second section for removal of a purified ethylene oxide exit stream.

12. The system of claim 11, where the liquid phase portion of the feed stream includes at least 35 percent of the ethylene oxide in the feed stream.

13. The system of claim 12, where the liquid phase portion of the feed stream includes at most 10 percent ethylene oxide, based on total weight of the liquid phase portion of the feed stream.

14. The system of claim 11, where the ethylene oxide, acetaldehyde, and other impurities in the liquid phase removed from the second section includes at least 60 percent of the acetaldehyde in the feed stream.

* * * * *